(12) United States Patent
Rizk et al.

(10) Patent No.: US 12,109,100 B2
(45) Date of Patent: *Oct. 8, 2024

(54) THREE-DIMENSIONAL RESORBABLE IMPLANTS FOR TISSUE REINFORCEMENT AND HERNIA REPAIR

(71) Applicant: Tepha, Inc., Lexington, MA (US)

(72) Inventors: Said Rizk, Windham, NH (US); Amit Ganatra, Attleboro, MA (US); Antonio Fosco, North Reading, MA (US); David P. Martin, Arlington, MA (US); Simon F. Williams, Cambridge, MA (US)

(73) Assignee: Tepha, Inc., Lexington, MA (US)

( * ) Notice: Subject to any disclaimer, the term of this patent is extended or adjusted under 35 U.S.C. 154(b) by 234 days.

This patent is subject to a terminal disclaimer.

(21) Appl. No.: 16/427,096

(22) Filed: May 30, 2019

(65) Prior Publication Data

US 2019/0314130 A1    Oct. 17, 2019

Related U.S. Application Data

(63) Continuation of application No. 14/687,435, filed on Apr. 15, 2015, now Pat. No. 10,335,257.
(Continued)

(51) Int. Cl.
*A61F 2/00* (2006.01)

(52) U.S. Cl.
CPC .... *A61F 2/0063* (2013.01); *A61F 2230/0093* (2013.01); *A61F 2240/004* (2013.01)

(58) Field of Classification Search
CPC ............ A61F 2/0063; A61F 2230/0093; A61F 2240/004
See application file for complete search history.

(56) References Cited

U.S. PATENT DOCUMENTS

| 5,116,357 A | 5/1992 | Eberbach |
| 5,368,602 A | 11/1994 | De La Torre |

(Continued)

FOREIGN PATENT DOCUMENTS

| EP | 2229918 | 9/2010 |
| EP | 2353545 | 8/2011 |

(Continued)

OTHER PUBLICATIONS

Martin, et al., "Medical applications of poly-4-hydroxybutyrate: a strong flexible absorbable biomaterial", Biochem. Eng. J., 16:97-105 (2003).

(Continued)

*Primary Examiner* — Alexander J Orkin
(74) *Attorney, Agent, or Firm* — Wolf, Greenfield & Sacks, P.C.

(57) ABSTRACT

Resorbable three-dimensional implants that can be temporarily deformed, implanted by minimally invasive means, and resume their original shape in vivo, have been developed. These implants are particularly suitable for use in minimally invasive procedures for tissue reinforcement, repair of hernias, and applications where it is desirable for the implant to contour in vivo to an anatomical shape, such as the inguinofemoral region. In the preferred embodiment, the implants are made from meshes of poly-4-hydroxybutyrate monofilament that have reinforced outlying borders that allow the meshes to form three-dimensional shapes that can be temporarily deformed. These implants can resume three-dimensional shapes after being temporarily deformed that contour to the host's tissue or an anatomical shape, for example, in the repair of a hernia, and particularly a hernia in the inguinofemoral region. The implants can contour to the host's tissue for example, of the inguinofemoral region, without the implants wrinkling, bunching or folding.

15 Claims, 4 Drawing Sheets

Related U.S. Application Data

(60) Provisional application No. 61/986,499, filed on Apr. 30, 2014.

(56) References Cited

U.S. PATENT DOCUMENTS

| | | | |
|---|---|---|---|
| 5,634,944 A | 6/1997 | Magram | |
| 5,766,246 A | 6/1998 | Mulhauser | |
| 5,811,272 A | 9/1998 | Snell | |
| 5,954,767 A | 9/1999 | Pajotin | |
| 6,245,107 B1 | 6/2001 | Ferree | |
| 6,287,316 B1 | 9/2001 | Agarwal | |
| 6,316,262 B1 | 11/2001 | Huisman | |
| 6,323,010 B1 | 11/2001 | Skraly | |
| 6,497,650 B1* | 12/2002 | Nicolo | A61F 2/0063 600/37 |
| 6,548,569 B1 | 4/2003 | Williams | |
| 6,610,764 B1 | 8/2003 | Martin | |
| 6,669,735 B1 | 12/2003 | Pelissier | |
| 6,723,133 B1 | 4/2004 | Pajotin | |
| 7,618,448 B2 | 11/2009 | Schmitz | |
| 7,641,825 B2 | 1/2010 | Rizk | |
| 8,016,883 B2 | 9/2011 | Coleman | |
| 8,034,270 B2 | 10/2011 | Martin | |
| 8,231,889 B2 | 7/2012 | Williams | |
| 8,287,909 B2 | 10/2012 | Martin | |
| 10,335,257 B2* | 7/2019 | Rizk | A61F 2/0063 |
| 2002/0062152 A1* | 5/2002 | Dauner | A61F 2/08 623/13.18 |
| 2002/0120348 A1* | 8/2002 | Melican | A61F 2/0045 623/23.72 |
| 2003/0130745 A1 | 7/2003 | Cherok | |
| 2003/0212460 A1 | 11/2003 | Darois | |
| 2003/0212462 A1 | 11/2003 | Gryska | |
| 2004/0234576 A1* | 11/2004 | Martin | B29C 71/0072 424/426 |
| 2005/0085924 A1* | 4/2005 | Darois | A61F 2/0063 623/23.74 |
| 2006/0064175 A1* | 3/2006 | Pelissier | A61F 2/0063 623/23.72 |
| 2009/0036996 A1* | 2/2009 | Roeber | D04B 21/16 623/23.72 |
| 2011/0144667 A1 | 6/2011 | Horton | |
| 2011/0152897 A1 | 6/2011 | Bates | |
| 2011/0288568 A1* | 11/2011 | Capuzziello | A61F 2/0063 606/151 |
| 2013/0197300 A1* | 8/2013 | Koullick | A61L 31/14 600/37 |
| 2014/0148827 A1* | 5/2014 | Odermatt | A61F 2/0063 606/151 |

FOREIGN PATENT DOCUMENTS

| | | |
|---|---|---|
| EP | 2586401 | 5/2013 |
| WO | 9932536 | 7/1999 |
| WO | 0058376 | 9/2000 |
| WO | 2006015276 | 2/2006 |
| WO | 2011119742 | 9/2011 |
| WO | 2011159784 | 12/2011 |
| WO | 2012064526 | 5/2012 |
| WO | 2013103862 | 7/2013 |

OTHER PUBLICATIONS

Martin, et al., "Characterization of poly-4-hydroxybutyrate mesdh for hernia repair applications", J Surg Res., 184:766-73 (2013).

Moore, et al., "Chemosynthesis of bioresorbable poly(gamma-butyrolactone) by ring-opening polymerization: a review", Biomaterials, 26:3771-82 (2005).

Williams, et al., "Poly-4-hydroxybutyrate (P4HB): a new generation of resorbable medical devices for tissue repair and regeneration", Biomed. Tech. 58(5):439-452 (2013).

International Search Report for PCT Application PCT/US2015/026005 mailed Jul. 16, 2015.

* cited by examiner

THREE-DIMENSIONAL RESORBABLE IMPLANTS FOR TISSUE REINFORCEMENT AND HERNIA REPAIR

CROSS-REFERENCE TO RELATED APPLICATIONS

This application is a continuation of U.S. Ser. No. 14/687,435, filed Apr. 15, 2015, which claims the benefit of and priority to U.S. Ser. No. 61/986,499, filed on Apr. 30, 2014, the disclosures of which are incorporated herein in their entirety.

FIELD OF THE INVENTION

The present invention generally relates to resorbable polymeric compositions that can be processed into fibers, converted into textile constructs such as knitted and woven meshes, and subsequently formed into three-dimensional shapes suitable for tissue reinforcement and hernia repair. The three-dimensional shapes may be temporarily deformed to allow their implantation by minimally invasive methods, and will then resume their original three-dimensional shape. The polymeric compositions include resorbable polyhydroxyalkanoates (PHA) polymers and copolymers, including poly-4-hydroxybutyrate and copolymers thereof.

BACKGROUND OF THE INVENTION

Mesh products made from non-resorbable fibers, such as polypropylene and polyester, are well known in the prior art, and widely used in hernia repair. Non-resorbable curved polypropylene meshes that can assume a curved shape are also now commonly used in hernia repair particularly for reinforcement of the inguinofemoral region. For example, U.S. Pat. Nos. 5,954,767, 6,368,541, 6,723,133 and 6,740,122 to Pajotin disclose curved knitted non-resorbable polypropylene meshes for repairing defects in muscle or tissue walls.

More recently, hernia repair products made from poly-4-hydroxybutyrate (P4HB) resorbable fibers have been disclosed by Martin et al. *J. Surg. Res.* 184:766-773 (2013), and are now used in the clinic. However, these resorbable products are either flat meshes or hernia repair plugs, and are not curved shapes that can be temporarily deformed, implanted, and released in vivo so that they conform to the anatomical shape, for example, of the inguinofemoral region.

There is thus a need to develop three-dimensional resorbable implants that can be temporarily deformed, implanted by minimally invasive methods, and that will resume their original three-dimensional shape after implantation, which also have the mechanical and physical properties suitable for use in plastic surgery and reconstruction.

It is an object of the present invention to provide resorbable three-dimensional implants that can be temporarily deformed, implanted by minimally invasive methods, and resume their original three-dimensional shape after implantation and contour to an anatomical shape.

It is a further object of the present invention to provide processes to produce resorbable three-dimensional implants that can be temporarily deformed from polyhydroxyalkanoate (PHA) and other resorbable polymers.

It is another object of the present invention to provide resorbable three-dimensional PHA implants that can be temporarily deformed that are made from monofilament and/or multifilament fibers of 4-hydroxybutyrate monomers or other resorbable polymeric monomers.

It is yet another object of the invention to provide resorbable three-dimensional implants, that can be temporarily deformed, and that are made from P4HB monofilament and/or multifilament meshes.

It is still another object of the invention to provide resorbable three-dimensional implants for use in tissue reinforcement and hernia repair that can be temporarily deformed, implanted by minimally invasive means, and resume their original shape in vivo and are designed to contour to the patient's host tissue or an anatomical shape.

It is still a further object of the invention to provide methods to implant resorbable three-dimensional implants that can be temporarily deformed to allow for minimally invasive delivery.

SUMMARY OF THE INVENTION

Resorbable three-dimensional implants that can be temporarily deformed, implanted by minimally invasive means, and resume their original shape in vivo, have been developed. These implants are particularly suitable for use in minimally invasive procedures for tissue reinforcement, the repair of hernias, and applications where it is desirable for the implant to contour in vivo to an anatomical shape, such as the inguinofemoral region. In the preferred embodiment, the implants are made from meshes of poly-4-hydroxybutyrate monofilament that have reinforced outlying borders that allow the meshes to form three-dimensional shapes that can be temporarily deformed. These implants can resume three-dimensional shapes after being temporarily deformed that contour to the host's tissue or an anatomical shape, for example, in the repair of a hernia, and particularly a hernia in the inguinofemoral region. The implants can contour to the host's tissue for example, of the inguinofemoral region, without the implants wrinkling, bunching or folding.

P4HB monofilament meshes can be molded into three-dimensional shapes that can be temporarily deformed, and will resume their original three-dimensional shape provided the outlying border of the three-dimensional shape has been reinforced. In a preferred embodiment, the outlying border is reinforced using a ring of unoriented P4HB fiber extrudate.

DETAILED DESCRIPTION OF THE INVENTION

Figure 1:
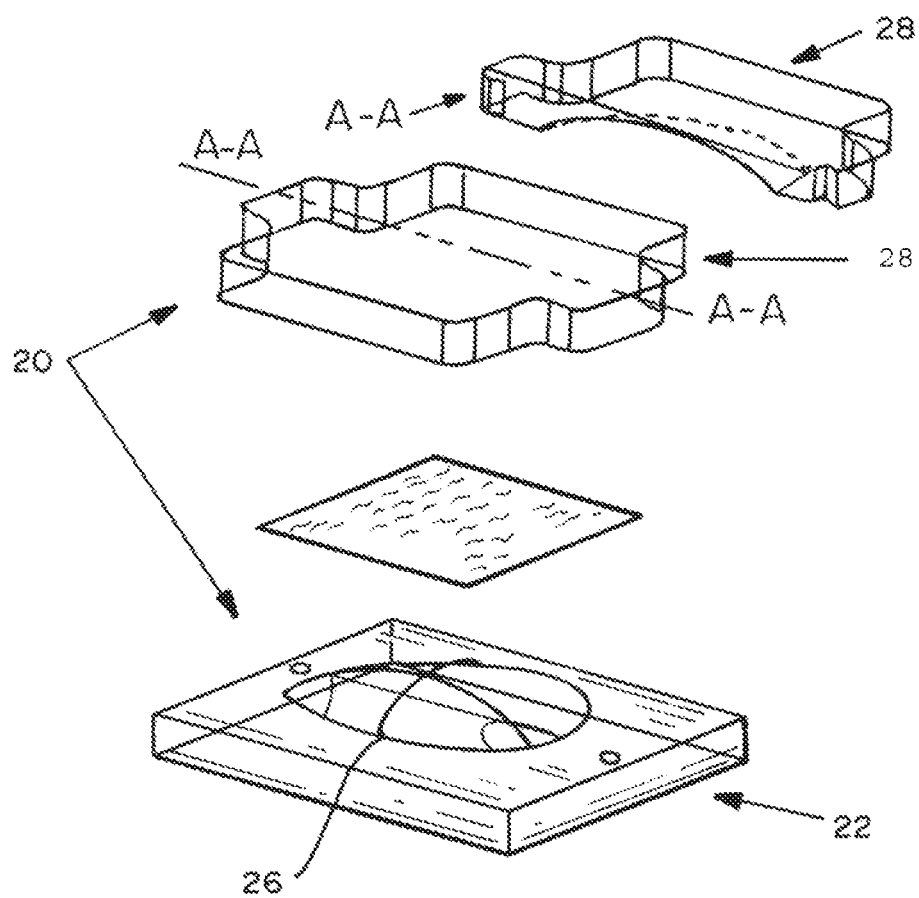
FIG. 1 is a diagram of a split metal form (20), consisting of an inwardly curving half (22) and a mating outwardly curving half (28) with a semicircular groove (26) in the outlying border of the inwardly curving half (22), which is used to make resorbable implants that can assume a three-dimensional shape unaided. A line (24) in the outwardly curving half (28) designated by the letters "AA" denotes the position of a cross-section with an arrow pointing at a separate view (28) of the cross-section.
Figure 2A:
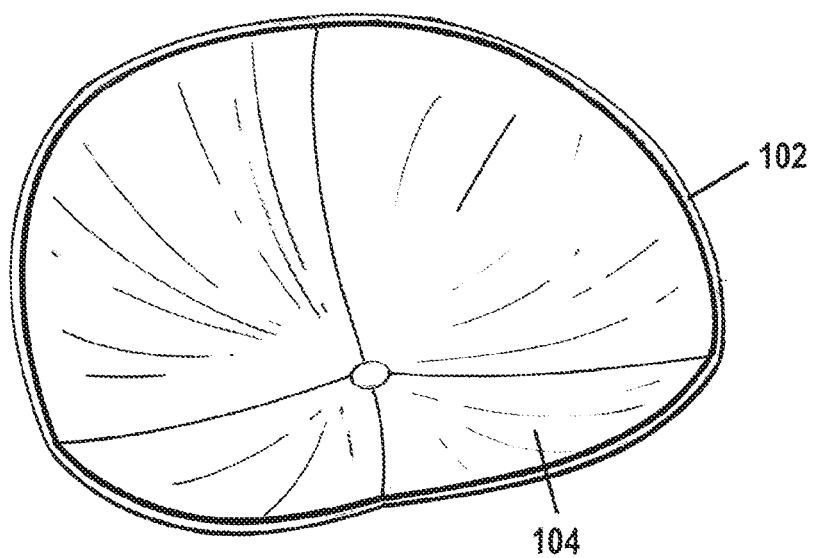
FIG. 2A depicts an implant (100) with a reinforced outlying border (102) and an outwardly curving exterior (104).
Figure 2B:
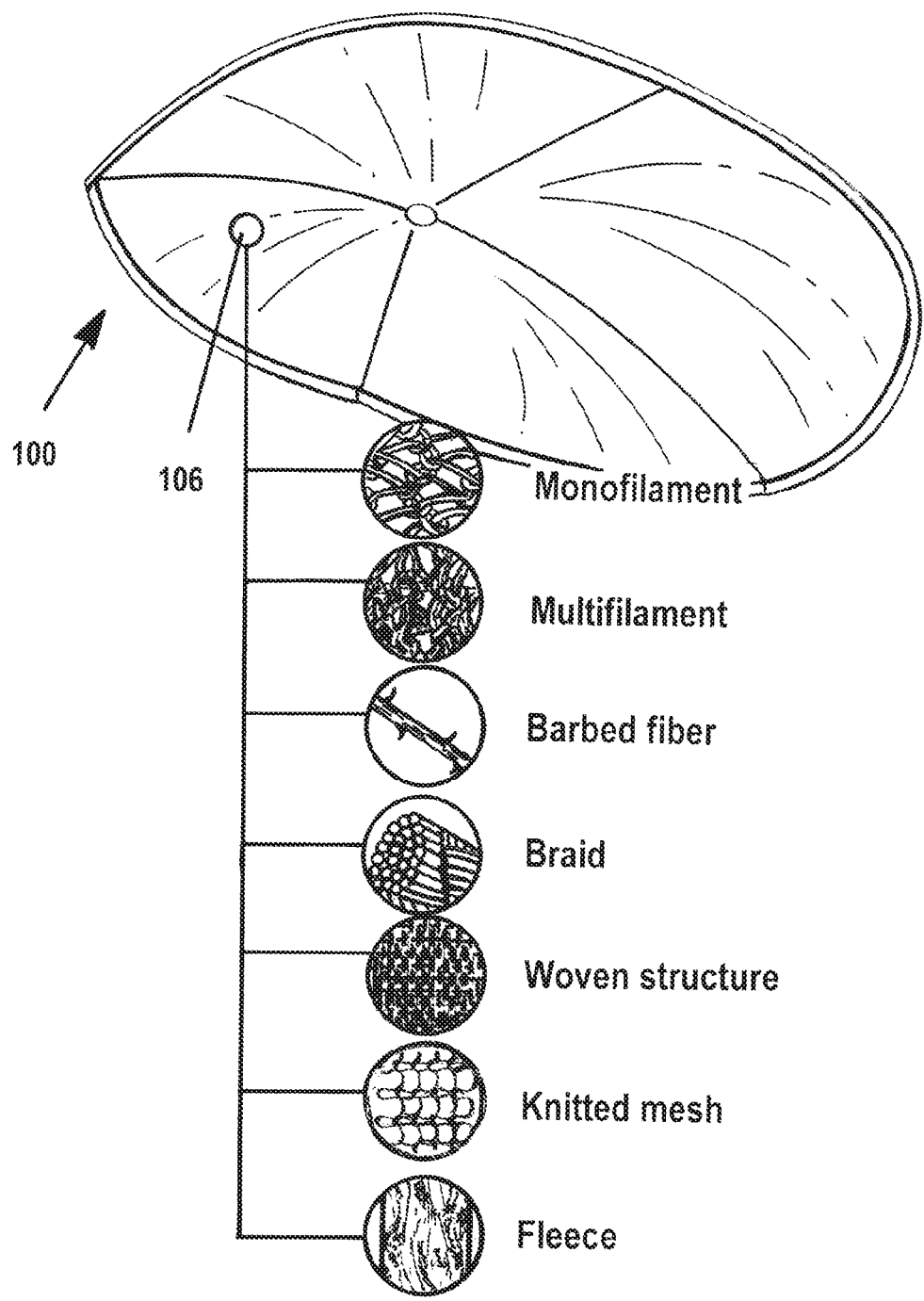
FIG. 2B depicts various embodiments of the implant (100) with a portion of the implant (106) expanded to show its composition.
Figure 3:
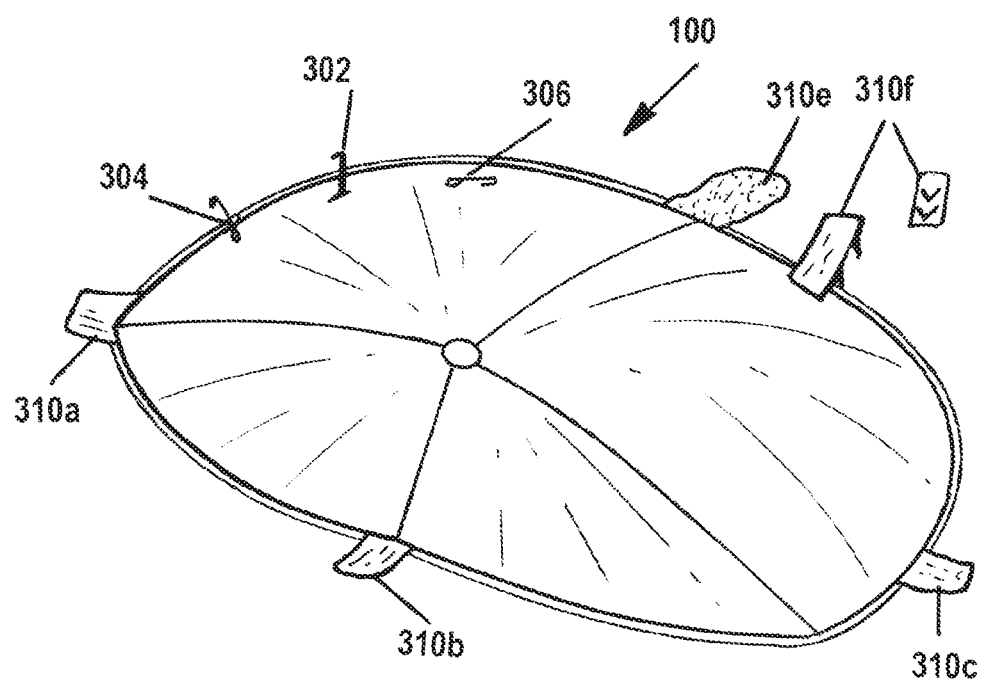
FIG. 3 depicts an implant (100) with attachment features such as tabs (310a, 310b, 310c, 310e and 310(f), hooks (302, 304), and staple (306).

Methods have been developed to prepare resorbable three-dimensional implants, from monofilament mesh, that can be temporarily deformed to allow implantation by minimally invasive methods. After implantation, the three-dimensional implants resume their original shape unaided, and can be designed so that they contour to the anatomical shape of the body. The resorbable three-dimensional implants are particularly useful when it is desirable for the implant to contour to the anatomical shape of the body without bunching, folding or wrinkling. For example, placement of a flat mesh in the inguinofemoral region to repair a hernia can result in a flat mesh wrinkling and slipping out of position. In contrast, a three-dimensional mesh can be designed to contour to the host's tissue, and even stay in place without the need for fixation.

The resorbable implants are preferably made from PHA polymers, and more preferably polymers of 4-hydroxybutyrate, and even more preferably from P4HB. Meshes made from monofilament and/or multifilament fibers of PHAs, such as 4HB, however have very different properties from meshes made from polypropylene fibers. Therefore methods that have been used, for example by Pajotin as disclosed in U.S. Pat. Nos. 5,954,767, 6,368,541, 6,723,133 and 6,740,122 are not adequate to create P4HB three-dimensional implants that can be temporarily deformed, implanted by a minimally invasive method, and are able to resume their original shape. This is primarily because polypropylene fibers are significantly stiffer than P4HB fibers, and have a lower elongation to break. Thus a mesh of polypropylene monofilament fibers can be molded into a three-dimensional shape, temporarily deformed, and upon release will resume its original three-dimensional shape. In contrast, when a mesh of P4HB fibers is molded into a three-dimensional shape and temporarily deformed, it will not resume its original three-dimensional shape.

The methods disclosed herein are based upon the discovery that P4HB monofilament meshes can be molded into three-dimensional shapes that can be temporarily deformed, and will resume their original three-dimensional shape provided the outlying border of the three-dimensional shape has been reinforced. In a preferred embodiment, the outlying border is reinforced using a ring of unoriented P4HB fiber extrudate.

I. Definitions

"Bioactive agent" is used herein to refer to therapeutic, prophylactic, and/or diagnostic agents. These include physiologically or pharmacologically active substances that act locally or systemically in the body. A biologically active agent is a substance used for, for example, the treatment, prevention, diagnosis, cure, or mitigation of one or more symptoms or characteristics of a disease or disorder, a substance that affects the structure or function of the body, or pro-drugs, which become biologically active or more active after they have been placed in a predetermined physiological environment. Bioactive agents include biologically, physiologically, or pharmacologically active substances that act locally or systemically in the human or animal body. Examples can include, but are not limited to, small-molecule drugs, peptides, proteins, sugars, polysaccharides, nucleotides, oligonucleotides, and nucleic acids molecules such as aptamers, siRNA, miRNA and combinations thereof.

"Biocompatible" as generally used herein means the biological response to the material or device is appropriate for the device's intended application in vivo. Metabolites of these materials should also be biocompatible.

"Blend" as generally used herein means a physical combination of different polymers, as opposed to a copolymer comprised of two or more different monomers.

"Burst strength" as used herein is determined by test method ASTM D6797-02 "Standard test method for bursting strength of fabrics constant rate of extension (CRE) ball burst test," using a MTS Q-Test Elite universal testing machine or similar device. The testing fixture uses a ⅜ inch diameter ball.

"Copolymers of poly-4-hydroxybutyrate" as generally used herein means any polymer which includes 4-hydroxybutyrate with one or more different hydroxyalkanoic acid units.

"Elongation" or "extensibility" of a material means the amount of increase in length resulting from, as an example, the tension to break a specimen. It is expressed usually as a percentage of the original length. (Rosato's Plastics Encyclopedia and Dictionary, Oxford Univ. Press, 1993).

"Molecular weight" as used herein, unless otherwise specified, refers to the weight average molecular weight (Mw), not number average molecular weight (Mn), and is measured by gel permeation chromatography (GPC) relative to polystyrene.

"Polyhydroxyalkanoates" or "PHAs" are linear polyesters produced by bacterial fermentation. Depending upon the microorganism and the cultivation conditions, homo- or copolyesters with different hydroxyalkanoic acids are generated.

"Poly-4-hydroxybutyrate" as generally used herein means a homopolymer of 4-hydroxybutyrate units. It may be referred to herein as P4HB or TephaFLEX® biomaterial (manufactured by Tepha, Inc., Lexington, MA). Polyhydroxybutyrate as generally used in the literature refers to the naturally occurring polymer poly-3-hydroxybutyrate.

"Reinforced" refers to a device formed of a material such as a P4HM that cannot be deformed and resume its pre-deformation shape, which contains a fiber, fibers, or region which causes the device to resume its pre-deformation shape following deformation. Examples of reinforcing materials are described below. These may be made of the same or different materials, wherein the reinforcement is caused by the composition or physical shape (suture, braid, weaving) of the reinforcing material.

"Resorbable" as generally used herein means the material is broken down in the body and eventually eliminated from the body. The terms "resorbable", "degradable", "erodible", and "absorbable" are used somewhat interchangeably in the literature in the field, with or without the prefix "bio". Herein, these terms will be used interchangeably to describe material broken down and gradually absorbed or eliminated by the body within five years, whether degradation is due mainly to hydrolysis or mediated by metabolic processes.

"Suture pullout strength" as used herein means the peak load (kg) at which an implant fails to retain a suture. It is determined using a tensile testing machine by securing an implant in a horizontal holding plate, threading a suture in a loop through the implant at a distance of 1 cm from the edge of the implant, and securing the suture arms in a fiber grip positioned above the implant. Testing is performed at a crosshead rate of 100 mm/min, and the peak load (kg) is recorded. The suture is selected so that the implant will fail before the suture fails. The suture pullout strength may be converted and expressed as Newtons.

"Taber Stiffness Unit" is defined as the bending moment of ⅕ of a gram applied to a 1½" (3.81 cm) wide specimen at a 5 centimeter test length, flexing it to an angle of 15°, and is measured using a Taber V-5 Stiffness Tester Model 150-B or 150-E. The TABER® V-5 Stiffness Tester—Model 150-B or 150-E is used to evaluate stiffness and resiliency properties of materials up to 10,000 Taber Stiffness Units. This precision instrument provides accurate test measurement to ±1.0% for specimens 0.004" to 0.219" thickness. One Taber Stiffness Unit is equal to 1 gram cm (g cm) or 0.0981 milliNewton meters (mN m). Taber Stiffness Units can be converted to Genuine Gurley™ Stiffness Units with the equation: $S_T=0.01419 S_G-0.935$, where $S_T$ is the stiffness in Taber Stiffness Units and $S_G$ is the stiffness in Gurley Stiffness Units. To convert Taber Stiffness Units to milliNewton Meters, use the equation: $X=S_T \cdot 0.098067$, where X is the stiffness in milliNewton Meters.

"Tensile modulus" is the ratio of stress to strain for a given material within its proportional limit.

II. Compositions

Methods have been developed to produce three-dimensional shapes from PHA compositions that can be temporarily deformed, and implanted using a minimally invasive method. After implantation, the three-dimensional shapes will resume their original shapes. The three-dimensional shapes are designed to contour to a patient's anatomy, and in particular to the anatomy of the inguinofemoral region.

A. Polymers

The methods described herein can typically be used to produce three-dimensional shapes from polyhydroxyalkanoates polymers, and more preferably from poly-4-hydroxybutyrate (P4HB) or a copolymer thereof. Copolymers include 4-hydroxybutyrate with 3-hydroxybutyrate, and 4-hydroxybutyrate with glycolic acid monomer. P4HB and copolymers thereof can be obtained from Tepha, Inc. of Lexington, MA Preferred PHA polymers have a weight average molecular weight (Mw) of 50,000 to 1,200,000, preferably 100,000 to 1,000,000 and more preferably, 100,000 to 800,000 based on gel permeation chromatography (GPC) relative to polystyrene standards.

Polyhydroxyalkanoates (PHAs) are produced by numerous microorganisms (see, for example, Steinbüchel A., et al. Diversity of Bacterial Polyhydroxyalkanoic Acids, *FEMS Microbial. Lett.* 128:219-228 (1995)). In nature these polyesters are produced as storage granules inside cells, and serve to regulate energy metabolism. They are also of commercial interest because of their thermoplastic properties, and relative ease of production.

Poly-4-hydroxybutyrate (P4HB) and copolymers thereof can be produced using transgenic fermentation methods, see, for example, U.S. Pat. No. 6,548,569 to Williams et al., and are produced commercially, for example, by Tepha, Inc. (Lexington, MA). P4HB is not naturally occurring. Poly-4-hydroxybutyrate (P4HB, TephaFLEX® biomaterial) is a strong, pliable thermoplastic polyester that, despite its biosynthetic route, has a relatively simple structure. Chemical synthesis of P4HB has been attempted, but it has been impossible to produce the polymer with a sufficiently high molecular weight that is necessary for most applications, including melt processing (see Hori, Y., et al., Polymer 36:4703-4705 (1995); Houk, K. N., et al., *J. Org. Chem.*, 2008, 73 (7), 2674-2678; and Moore, T., et al., *Biomaterials* 26:3771-3782 (2005)). In fact, it has been calculated to be thermodynamically impossible to chemically synthesize a high molecular weight homopolymer under normal conditions (Moore, T., et al., *Biomaterials* 26:3771-3782 (2005)). Chemical synthesis of P4HB instead yields short chain oily oligomers that lack the desirable thermoplastic properties of the high molecular weight P4HB polymers produced by biosynthetic methods.

It should be noted that the literature commonly refers to another polyhydroxyalkanoate, poly-3-hydroxybutyrate (P3HB), simply as polyhydroxybutyrate (PHB) (see Section 2 of Moore, T., et al., *Biomaterials* 26:3771-3782 (2005)). PHB has entirely different properties to P4HB. It is structurally and functionally different to P4HB. For example, PHB has a melting point of 180° C. versus a melting point of about 61° C. for P4HB. The polymers also have substantially different glass transition temperatures and mechanical properties. For example, PHB is a relatively hard brittle polymer with an extension to break of just a few percent, whereas P4HB is a strong extensible polymer with an extension to break of about 1000%. Substantially different conditions are required to process these two polymers, and the resulting products have substantially different properties.

U.S. Pat. Nos. 6,245,537, 6,623,748, 7,244,442, and 8,231,889 describe methods of making PHAs with little to no endotoxin, which are suitable for medical applications. U.S. Pat. Nos. 6,548,569, 6,838,493, 6,867,247, 7,268,205, 7,179,883, 7,268,205, 7,553,923, 7,618,448 and 7,641,825 and WO 2012/064526 describe use of PHAs to make medical devices. Copolymers of P4HB include 4-hydroxybutyrate copolymerized with 3-hydroxybutyrate or glycolic acid (U.S. Pat. No. 8,039,237 to Martin and Skraly, U.S. Pat. No. 6,316,262 to Huisman et al., and U.S. Pat. No. 6,323,010 to Skraly et al.). Methods to control molecular weight of PHA polymers have been disclosed by U.S. Pat. No. 5,811,272 to Snell et al.

PHAs with controlled degradation and degradation in vivo of less than one year are disclosed by U.S. Pat. Nos. 6,548,569, 6,610,764, 6,828,357, 6,867,248, and 6,878,758 to Williams et al. and WO 99/32536 to Martin et al. Applications of P4HB have been reviewed in Williams, S. F., et al., *Polyesters, III*, 4:91-127 (2002), Martin, D. et al. Medical Applications of Poly-4-hydroxybutyrate: A Strong Flexible Absorbable Biomaterial, *Biochem. Eng. J.* 16:97-105 (2003), and Williams, S. et al. Poly-4-hydroxybutyrate (P4HB): a new generation of resorbable medical devices for tissue repair and regeneration, *Biomed. Tech. (Berl)* ISSN (Online) 1862-278X, ISSN (Print) 0013-5585, DOI: 10.1515/bmt-2013-0009, 2013. Medical devices and applications of P4HB have also been disclosed by WO 00/56376 to Williams et al. Several patents including U.S. Pat. Nos. 6,555,123, 6,585,994, and 7,025,980 to Williams and Martin describe the use of PHAs in tissue repair and engineering. WO 2007/092417 to Rizk et al. discloses compositions of PLA (polylactic acid) toughened with P4HB suitable for medical applications.

WO 04/101002 to Martin, et al., U.S. Pat. No. 8,034,270 to Martin et al., U.S. Pat. No. 8,016,883 to Coleman et al., and U.S. Pat. No. 8,287,909 to Martin et al., WO 2011/119742 to Martin et al., WO 06/015276 to Rizk, and WO 2011/159784 to Cahil et al. disclose fibers, non-wovens, and textiles made by melt extrusion of P4HB. However, none of these disclosures describe three-dimensional shapes that can be temporarily deformed, implanted using minimally invasive methods, and reopened to their original shapes to conform to anatomical structures. These disclosures also do not describe processes that would be adequate to form such shapes that can be temporarily deformed, and reopen to their original shapes unaided.

If desired, the PHA polymer may be blended with another PHA polymer prior to processing, or blended with a non-PHA material, including other absorbable biocompatible polymers, dyes and bioactive agents (such as drug molecules or other therapeutic, prophylactic or diagnostic agents). Other absorbable biocompatible polymers in any form, including fibers, may also be incorporated into the three-dimensional shapes to form hybrid structures. Other absorbable biocompatible polymers, include, but are not limited to, poly(lactides); poly(glycolides); poly(lactide-co-glycolides); poly(lactic acid); poly(glycolic acid); poly(lactic acid-co-glycolic acids); polycaprolactones; poly(orthoesters); polyanhydrides; poly(phosphazenes); synthetically or biologically prepared polyesters (including polyesters with one or more of the following monomeric units: glycolic, lactic; trimethylene carbonate, p-dioxanone, or ε-caprolactone); poly(lactide-co-caprolactones); polycarbonates; tyrosine polycarbonates; polyamides (including synthetic and natural polyamides, polypeptides, and poly(amino acids)); polyesteramides; poly(dioxanones); poly(alkylene alkylates); polyethers (such as polyethylene glycol, PEG, and polyethylene oxide, PEO); polyvinyl pyrrolidones or PVP; polyurethanes; polyetheresters; polyacetals; polycyanoacrylates; poly(oxyethylene)/poly(oxypropylene) copolymers; polyacetals, polyketals; polyphosphates; (phosphorous-containing) polymers; polyphosphoesters; polyalkylene oxalates; polyalkylene succinates; poly(maleic acids); chitin; chitosan; modified chitosan; collagen; silk; biocompatible polysaccharides; biocompatible copolymers (including block copolymers or random copolymers); hydrophilic or water soluble polymers, such as polyethylene glycol, (PEG) or polyvinyl pyrrolidone (PVP), with blocks of other biocompatible or biodegradable polymers, for example, poly (lactide), poly(lactide-co-glycolide, or polycaprolcatone or combinations thereof. In some embodiments the implant includes hyaluronic acid or derivative thereof, collagen, hydroxyapatite, or absorbable polymer with one or more the following monomeric units: glycolic acid, lactic acid, trimethylene carbonate, p-dioxanone, and caprolactone.

In one embodiment, the implants include one or more of the following: dye, medical marker, contrast agent, radiopaque marker, radioactive substance.

B. Additives

Certain additives may be incorporated into P4HB, copolymers and blends thereof prior to converting these compositions into three-dimensional structures. Preferably, these additives are incorporated during the compounding process to produce pellets that can be subsequently processed into fibers suitable for making the three-dimensional shapes. In another embodiment, the additives may be incorporated using a solution-based process. In a preferred embodiment, the additives are biocompatible, and even more preferably the additives are both biocompatible and resorbable.

In one embodiment, the additives may be nucleating agents and/or plasticizers. These additives may be added in sufficient quantity to produce the desired result. In general, these additives may be added in amounts of up to 20% by weight. Nucleating agents may be incorporated to increase the rate of crystallization of the P4HB homopolymer, copolymer or blend. Such agents may be used to improve the mechanical properties of fibers and meshes, and to reduce cycle times. Preferred nucleating agents include, but are not limited to, salts of organic acids such as calcium citrate, polymers or oligomers of PHA polymers and copolymers, high melting polymers such as PGA, talc, micronized mica, calcium carbonate, ammonium chloride, and aromatic amino acids such as tyrosine and phenylalanine.

Plasticizers that may be incorporated into the compositions include, but are not limited to, di-n-butyl maleate, methyl laureate, dibutyl fumarate, di(2-ethylhexyl) (dioctyl) maleate, paraffin, dodecanol, olive oil, soybean oil, polytetramethylene glycols, methyl oleate, n-propyl oleate, tetrahydofurfuryl oleate, epoxidized linseed oil, 2-ethyl hexyl epoxytallate, glycerol triacetate, methyl linoleate, dibutyl fumarate, methyl acetyl ricinoleate, acetyl tri(n-butyl) citrate, acetyl triethyl citrate, tri(n-butyl) citrate, triethyl citrate, bis(2-hydroxyethyl) dimerate, butyl ricinoleate, glyceryl tri-(acetyl ricinoleate), methyl ricinoleate, n-butyl acetyl rincinoleate, propylene glycol ricinoleate, diethyl succinate, diisobutyl adipate, dimethyl azelate, di(n-hexyl) azelate, tri-butyl phosphate, and mixtures thereof. Particularly preferred plasticizers are citrate esters.

In another preferred embodiment, the additives are contrast agents, radiopaque markers and radioactive substances. These additives may also be incorporated into the P4HB homopolymer, copolymer or blend either before preparing fibers and meshes that are molded into three-dimensional shapes or after they are prepared.

C. Bioactive Agents

If desired, the P4HB homopolymer and copolymers thereof used to make the three-dimensional shapes may incorporate bioactive agents. These bioactive agents may be added during the formulation process, during pelletization or blending, or may be added later to the fibers or meshes.

In one embodiment, the bioactive agents, the P4HB polymer, copolymer, or blend, may be dissolved in a solvent or solvent system in order to disperse the bioactive agent in the P4HB polymer, copolymer or blend, and the solvent may then be removed by evaporation. Preferred solvents include methylene chloride, chloroform, tetrahydrofuran, acetone, dimethylformamide, and 1,4-dioxane.

Examples of bioactive agents that can be incorporated into the P4HB polymer, copolymer, or blends thereof, include, but are not limited to, small-molecule drugs, anti-inflammatory agents, immunomodulatory agents, molecules that promote cell migration, molecules that promote or retard cell division, molecules that promote or retard cell proliferation and differentiation, molecules that stimulate phenotypic modification of cells, molecules that promote or retard angiogenesis, molecules that promote or retard vascularization, molecules that promote or retard extracellular matrix disposition, signaling ligands, platelet rich plasma, anesthetics, hormones, antibodies, growth factors, extracellular matrix or components thereof (fibronectin, laminin, vitronectin), integrins, antibiotics, steroids, hydroxyapatite, silver particles, vitamins, non-steroidal anti-inflammatory drugs, chitosan and derivatives thereof, alginate and derivatives thereof, collagen, hyaluronic acid and derivatives thereof, allograft material, xenograft material, and ceramics. Representative materials include proteins, peptides, sugars, polysaccharides, nucleotides, oligonucleotides, lipids, lipoproteins, nucleic acid molecules such as antisense molecules, aptamers, siRNA, and combinations thereof.

III. Three-Dimensional PHA Implants and Methods of Manufacturing

A. Fibers for Making Three-Dimensional PHA Medical Devices

In a preferred embodiment, the three-dimensional shapes are formed of P4HB monofilament meshes. The P4HB monofilament fibers used to make these meshes may be prepared by melt extrusion or solution spinning. The P4HB monofilament fibers are made by melt extrusion, for example, as described by WO 2011/119742 to Martin et al. and U.S. Pat. No. 8,034,270 to Martin et al.

The diameters of the P4HB monofilament fibers may range from 10 µm to 1 mm, but more preferably have a diameter ranging from 50 µm to 600 µm, and even more preferably from 50 µm to 250 µm. In a preferred embodiment, the P4HB monofilament fibers are oriented. The exact mechanical properties of the fibers will depend upon the degree of orientation. In a particularly preferred embodiment, the oriented P4HB monofilament fibers will have one or more of the following properties: a tensile strength of at least 100 MPa, more preferably at least 300 MPa, and even more preferably at least 500 MPa; an elongation to break of less than 500%, more preferably less than 300%, and even more preferably less than 100%; a tensile modulus of at least 100 MPa, more preferably at least 300 MPa, and even more preferably at least 500 MPa.

In another embodiment, the three-dimensional shapes comprise P4HB multifilament fibers. P4HB multifilament fibers may be prepared by melt extrusion or solution spinning. In a preferred embodiment, the P4HB multifilament fibers are made by melt extrusion, and may be prepared as described by WO 2011/119742 to Martin et al. and U.S. Pat. No. 8,034,270 to Martin et al. In an embodiment the P4HB multifilament fibers are prepared with a denier per filament (dpf) of less than 6, more preferably less than 4, and even more preferably less than 3. In another embodiment, the multifilament fibers are prepared with a tenacity of greater than 2 gram/denier, and more preferably greater than 4 gram/denier.

B. Methods of Making PHA Meshes

In a preferred embodiment, the three-dimensional shapes include P4HB monofilament meshes. Suitable P4HB monofilament meshes may be made as disclosed by WO 2011/119742 to Martin et al. and U.S. Pat. No. 8,034,270 to Martin et al.

In an embodiment, the PHA meshes have one or more of the following properties: a suture pullout strength of at least 10 N, and more preferably at least 20 N; a burst strength of at least 1 Kg, more preferably at least 10 Kg, and even more preferably at least 20 Kg; pore diameters that are at least 50 µm, more preferably at least 100 µm, and even more preferably over 250 µm; and a Taber stiffness that is less than 100 Taber stiffness units, and more preferably less than 10 Taber stiffness units.

In a preferred embodiment, the PHA mesh is made from P4HB monofilament fiber. In a more preferred embodiment, the P4HB monofilament mesh has a knitted or woven structure. A particularly preferred P4HB monofilament mesh has substantially one or more of the following properties: a pore diameter of approximately 500 µm, thickness of 0.5 mm, areal density of approx. 182 $g/m^2$, suture pullout strength of 5.6 kgf, and a burst strength of 24.5 Kg.

In another embodiment, the PHA meshes may comprise different sized fibers or other non-PHA fibers, including PHA multifilament, and fibers made from other absorbable or non absorbable biocompatible polymers and hybrid meshes.

C. Method of Coating PHA Meshes

In an embodiment, the PHA meshes may be coated with other substances, such as additives and bioactive agents. The coatings may range from a thin coating on the surface of a PHA fiber to complete coverage or encapsulation of a PHA mesh. The additives and bioactive agents may be applied directly or first suspended or dissolved in a carrier, such as another polymer. In a preferred embodiment, the PHA meshes may be coated with collagen.

D. Fabrication of Three-Dimensional PHA Implants

PHA polymers and copolymers possess properties that are useful for preparing three-dimensional implants that can be temporarily deformed to facilitate minimally invasive delivery, and contour to the patient's tissues or be shaped into anatomical forms once delivered in vivo. These implants may be used, for example, in hernia repair and tissue reinforcement. The disclosed structures of PHA polymers and copolymers allow the implants to be deformed and subsequently assume three-dimensional shapes unaided. The three-dimensional implants may be placed without the need for fixation, reducing cost, and eliminating the chance of nerve entrapment. In contrast, flat mesh must be fixated to prevent it from moving. Because the three-dimensional implants are designed for easy positioning by contouring to the patient's anatomy, excessive folding and wrinkling that can occur in placing flat implants is eliminated. In a particularly preferred embodiment, the three-dimensional implants are formed and shaped for the inguinal anatomy, and may be used for the laparoscopic repair of inguinal hernias.

In an embodiment, the three-dimensional PHA implants are prepared by molding. In these processes, PHA polymer or copolymer textile structures, such as P4HB monofilament meshes, are molded into a three-dimensional implant. In a preferred embodiment, three-dimensional shapes are prepared by molding a monofilament mesh of a PHA polymer or copolymer into a shape designed to contour to the host's tissue. In a particularly preferred embodiment, the shape is designed for hernia repair. Such shapes include those with an outwardly curving exterior and inwardly curving interior, and optionally contain an outlying border that is reinforced by a continuous or interrupted ring that allows the scaffold to assume a three-dimensional shape unaided after being temporarily deformed. Shapes with outwardly curving exteriors and inwardly curving interiors may, for example, be prepared using a split metal form consisting of an inwardly curving half and a mating outwardly curving half as shown in FIG. 1. One skilled in the art will understand that the size and shape of the split metal form can be varied in order to provide different three-dimensional shapes that contour to the specific needs of a patient. In a preferred embodiment, the inwardly curving half of the metal form contains a semicircular groove in the outlying border that will accommodate a continuous or interrupted ring of filament, thread, strand, string, fiber, yarn, wire, film, tape, tube, fabric, felt, mesh, multifilament, monofilament, or fiber extrudate. In a particularly preferred embodiment the groove will accommodate a monofilament, preferably a monofilament extrudate. The semicircular groove is cut into the outlying border of the inwardly curving half such that the ring of material, for example, a monofilament, will protrude from the groove. In an alternative embodiment, the groove may be cut into the outwardly curving half instead of the inwardly curving half. A three-dimensional shape with an inwardly curving interior, outwardly curving exterior, and reinforced outlying border is prepared by placing, for example, a monofilament extrudate in the semicircular groove of the inwardly curving half so that it forms a ring, draping a polymeric material such as a monofilament mesh over the inwardly curving half of the metal form, placing the mating outwardly curving half of the metal form over the polymeric material, and clamping the two halves of the split metal form together to form a block. The block is then heated, cooled, disassembled, and the three-dimensional shape removed and trimmed as necessary to form a smooth outlying border. In an embodiment, the block is heated uniformly, preferably by heating with hot water or other heating media, and cooled uniformly, preferably by cooling with ambient temperature water. In a preferred embodiment, the three-dimensional shape is made from a poly-4-hydroxybutyrate monofilament mesh, and a poly-4-hydroxybutyrate monofilament extrudate. The temperature of the hot water is set such that the ring is either pressed or melted into the outlying border to reinforce the outlying border. When the three-dimensional shape is made from poly-4-hydroxybutyrate, the temperature of the hot water is set at approximately 56° C., and the polymer construct is heated for approximately 5 minutes. It has been discovered that if a ring of polymer, derived, for example, from a poly-4-hydroxybutyrate monofilament extrudate, is used to reinforce the outlying border of the poly-4-hydroxybutyrate mesh, the mesh will be able to assume a three-dimensional shape unaided after being temporarily deformed. The ring may be melted into the mesh as described above, or welded, using, for example, sonic welding, or otherwise attached to the formed mesh. However, if a ring is not used to reinforce the edge of the poly-4-hydroxybutyrate material (such as a monofilament mesh), the poly-4-hydroxybuyrate material will not be able to assume a three-dimensional shape unaided after being temporarily deformed.

Three-dimensional shapes that can be temporarily deformed may also be prepared from porous P4HB films instead of fibers. For example, P4HB films may be prepared by melt extrusion or solution spinning. These films may be oriented, and then drilled or fibrillated to produce mesh like P4HB porous film structures. The latter may be reinforced by a continuous or interrupted ring of filament, thread, strand, string, fiber, yarn, wire, film, tape, tube, fabric, felt, mesh, multifilament, monofilament, or fiber extrudate, so that they will assume a three-dimensional shape that can be temporarily deformed.

In an embodiment, the three-dimensional implants can incorporate one or more tabs or straps (attachment sites) to accommodate suture throws or other anchoring devices, such as tacks, hooks, and pins, for the fixation of the implant to the patient's tissues. The three-dimensional implants can also incorporate sutures, with or without needles, for the fixation of the implant to the patient's tissues. These tabs and sutures can be placed in order to improve the implant's ability to contour to the host's tissue, or to form an anatomical shape. In particular, these tabs and sutures can be incorporated with appropriate spacing into the implant so that they prevent migration of the implant. The tabs and sutures can also be incorporated to prevent the implant from bunching, kinking, folding or wrinkling.

In another embodiment, the three-dimensional implants can be self-anchoring. Preferably, the three-dimensional self-anchoring implants incorporate a self-fixating system on the side of the implant that contacts with the patient's tissue. The three-dimensional self-anchoring implants can be made, for example, from a textile or film, such as a self-anchoring knitted or woven mesh. In an embodiment, a self-anchoring textile can be prepared, for example, with barbs, fleece, or self-fixating tips, or with micro grips. In one embodiment, a self-anchoring mesh may be prepared by shaving half loops from a looped knitted mesh on the anchoring side of a three-dimensional implant. In another embodiment, a self-anchoring mesh may be prepared from more than one fiber by inserting loops of heavier stiffer fiber during the knitting process or stitching loops into a pre-formed mesh, and then shaving those loops to form barb like surfaces. In a further embodiment, self-anchoring three-dimensional implants may be prepared using a laser to cut the anchoring side of the implant to provide a plurality of tissue engaging barbs. In a preferred embodiment, the self-anchoring three-dimensional implants are made from poly-4-hydroxybutyrate, and more preferably from monofilaments thereof. In an even more preferred embodiment, the self-anchoring three-dimensional implants are made from a poly-4-hydroxybutyrate knitted mesh wherein the self-anchoring side of the mesh has been treated to form barbs, fleece, self-fixating tips, or micro grips, for example, by shaving half loops or cutting with a laser or mechanical instrument.

The three-dimensional implants may be sterilized using ethylene oxide, gamma-irradiation, or electron beam radiation (e-beam). In a preferred embodiment, P4HB implants are sterilized using ethylene oxide, and packaged.

IV. Methods of Delivery of Three-Dimensional PHA Implants

In a preferred embodiment, the implants described herein that can assume a three-dimensional shape unaided after being temporarily deformed are implanted using minimally invasive techniques. These implants may, for example, be rolled up into a small cylindrical shape, placed inside a tubular inserter, and implanted through a small incision. Once released in vivo, these implants will assume their three-dimensional shapes unaided, and may be moved into position, for example, to contour to the host's tissue (or form an anatomical shape) for use in hernia repair or tissue reinforcement. In a preferred embodiment, the implants are designed so that they will stretch in both directions to accommodate and reinforce tissue defects. The three-dimensional implants may also incorporate one or more medical markers to aid the surgeon in orientation of the implant.

One skilled in the art will appreciate that these three-dimensional implants can also be delivered by other minimally invasive methods as well as using more traditional open surgery techniques.

The present invention will be further understood by reference to the following non-limiting examples.

Example 1: Preparation of P4HB Monofilament by Melt Extrusion

Bulk P4HB resin in pellet form was dried to less than 300 ppm water using a rotary vane vacuum pump system. The dried resin was transferred to an extruder feed hopper with nitrogen purge to keep the pellets dry. The pellets were gravity fed into a chilled feeder section and introduced into the extruder barrel, which was 1.50 inches in diameter and fitted with an extrusion screw with a 30:1 L/D ratio. The extruder barrel contained 5 heating zones (or extrusion zones)—zones 1, 2, 3, 4 and 5, and was manufactured by American Kuhne. The heated and softened resin from the extruder was fed into a heated metering pump (melt pump) and from the melt pump the extruded resin was fed into the heated block and an eight hole spinneret assembly. Processing profile ranges from 40° C. to 260° C. for temperatures, and 400 psi to 2000 psi for pressures, were used. The molten filaments were water quenched and conveyed into a three-stage orientation, with inline relaxation, before winding of the monofilaments on spools. Test values for extruded monofilament fiber are shown in Table 1.

TABLE 1

Mechanical Test Data for P4HB Monofilament Fiber

| Fiber USP Size | Diameter, mm | Breaking Strength, Kg | Break Elongation |
|---|---|---|---|
| 5/0 | 0.150 | 1.80 | 30% |
| 6/0 | 0.100 | 1.00 | 29% |

Example 2: Preparation of a P4HB Monofilament Mesh

Spools with P4HB monofilament fiber prepared as described in Example 1 were converted into P4HB monofilament mesh as follows: Monofilament fibers from 49 spools were mounted on a creel, aligned side by side and pulled under uniform tension to the upper surface of a "kiss" roller. The "kiss" roller was spinning while semi-immersed in a bath filled with a 10% solution of TWEEN® 20 lubricant. The TWEEN® 20 lubricant was deposited on the surface of the sheet of fiber. Following the application of TWEEN® 20, the sheet of fiber was passed into a comb guide and then wound on a warp beam. A warp is a large wide cylinder onto which individual fibers are wound in parallel to provide a sheet of fibers. Next, warp beams were converted into a finished mesh fabric by means of interlocking knit loops. Eight warp beams were mounted in parallel onto tricot machine let-offs and fed into the knitting elements at a constant rate determined by the 'runner length'. Each individual monofilament fiber from each beam was fed through a series of dynamic tension elements down into the knitting 'guides'. Each fiber was passed through a single guide, which was fixed to a guide bar. The guide bar directed the fibers around the needles forming the mesh fabric structure. The mesh fabric was then pulled off the needles by the take down rollers at a constant rate of speed determined by the fabric 'quality'. The mesh fabric was then taken up and wound onto a roll ready for scoring.

Example 3: Scouring of P4HB Monofilament Mesh and Cytotoxicity Testing

The P4HB monofilament mesh produced according to the method of Example 2 was scored ultrasonically with water, heat set in hot water, and then washed with a 70% aqueous ethanol solution. Cytotoxicity testing of two grams of the mesh was undertaken using the ISO Elution Method (1×MEM Extract) following the guidelines of the International Organization for Standardization 10993: Biological Evaluation of Medical Devices, Part 5: Tests for Cytotoxicity: in vitro Methods. The scoured P4HB monofilament mesh passed the cytotoxicity testing.

Example 4: Preparation of a P4HB Implant from an Absorbable Monofilament Mesh that Unaided Assumes a Three-Dimensional Shape Designed to Contour to a Patient's Tissue for Hernia Repair A split metal mold (see FIG. 1) consisting of an inwardly curving half and a mating outwardly curving half, with a semicircular groove placed in the outlying border of the inwardly curving half was prepared. A P4HB monofilament extrudate was extruded, cut to length, and pushed into the semicircular groove with part of the monofilament protruding from the groove. A knitted P4HB monofilament mesh, measuring approx. 15×20 cm, with a pore diameter of approximately 500 µm, thickness of 0.5 mm, areal density of approx. 182 g/m², suture pullout strength of 5.6 kgf, and a burst strength of 24.5 Kg, was draped over the entire surface of the inwardly curving half of the metal form and the monofilament in the semicircular groove. The mating outwardly curving metal form was gently placed over the mesh, and the two halves of the split metal mold were clamped together to form a block. The block was uniformly heated on all sides by placing the block in hot water maintained at 56° C. for 5 minutes. The block was then uniformly cooled for 1 to 2 minutes by placing the block into a water bath at ambient temperature. The block was disassembled, and the three-dimensional mesh gently lifted from the metal mold. Unwanted compressed extrudate was removed from the implant by trimming the outlying border.

Example 5: Minimally Invasive Delivery of a Three-Dimensional P4HB Implant

The three-dimensional implant prepared in Example 4 was rolled into a small diameter cylinder, and placed inside an insertion device suitable for deployment of the implant in vivo.

The implant immediately assumed its three-dimensional shape unaided when the implant was deployed from the insertion device.

Example 6: Preparation of a P4HB Implant with an Absorbable Monofilament Mesh with a Three-Dimensional Shape without a Reinforced Outlying Border for Comparison with Example 4

A split metal mold (see FIG. 1) consisting of an inwardly curving half and a mating outwardly curving half was prepared, but without a semicircular groove placed in the outlying border of the inwardly curving half was prepared. A knitted P4HB monofilament mesh, measuring approx. 15×20 cm, with a pore diameter of approximately 500 µm, thickness of 0.5 mm, areal density of approx. 182 g/m², suture pullout strength of 5.6 kgf, and a burst strength of 24.5 Kg, was draped over the entire surface of inwardly curving half of the metal form. The mating outwardly curving metal form was gently placed over the mesh, and the two halves of the split metal mold were clamped together to form a block. The block was uniformly heated on all sides by placing the block in hot water maintained at 56° C. for 5 minutes. The block was then uniformly cooled for 1 to 2 minutes by placing the block into a water bath at ambient temperature. The block was disassembled, and the three-dimensional mesh gently lifted from the metal mold. Unwanted mesh was removed from the implant by trimming.

Example 7: Attempted Minimally Invasive Delivery of a Three-Dimensional P4HB Implant without a Reinforced Outlying Border for Comparison with Example 5

The implant prepared in Example 6 was rolled into a small diameter cylinder, and placed inside an insertion device suitable for deployment of the implant in vivo.

The implant failed to assume its three-dimensional shape unaided when the implant was deployed from the insertion device. This example demonstrates the need to reinforce the outlying border of a three-dimensional P4HB implant in order for the implant to assume its original shape unaided after being temporarily deformed.

Modifications and variations of the invention described herein will be obvious to those skilled in the art and are intended to come within the scope of the appended claims.

We claim:

1. A porous implant consisting of:
a self-anchoring patch to position over a muscle or tissue wall defect, the patch comprising a textile fabricated with first and second fibers of poly-4-hydroxybutyrate or copolymer thereof, wherein the first fiber used to fabricate the patch is stiffer than the second fiber used to fabricate the patch, the textile having a first side and a second side, wherein the first fiber is on at least one of the first side and the second side of the textile, wherein the first fiber is configured to self-anchor the patch to muscle or tissue, and wherein the first side comprises a first exposed surface extending across a central portion of the first side, and the second side comprises a second exposed surface extending across a central portion of the second side, the first and second exposed surfaces facing in opposite directions.

2. The implant of claim 1, wherein the textile is a mesh, monofilament mesh, multifilament mesh, woven mesh, knitted mesh, braid or mesh comprising a barbed suture.

3. The implant of claim 1, wherein the first fiber comprises one or more of the following: barbs, fleece, micro grips, hooks, anchoring devices, shaved half-loops, and self-fixating tips.

4. The implant of claim 1, wherein the first fiber is on the second side of the textile.

5. The implant of claim 1, wherein the first fiber includes a plurality of tissue engaging barbs.

6. The implant of claim 1, wherein the patch further comprises one or more of the following: plasticizer, nucleant, dye, medical marker, bioactive agent, therapeutic agent, diagnostic agent, prophylactic agent, contrast agent, radiopaque marker, radioactive substance, hyaluronic acid or derivative thereof, collagen, hydroxyapatite, or an absorbable polymer comprising one or more of the following monomeric units: glycolic acid, lactic acid, trimethylene carbonate, p-dioxanone, and caprolactone.

7. The implant of claim 1, wherein the patch is packaged and sterilized using ethylene oxide, gamma-irradiation or electron beam radiation.

8. The implant of claim 1, wherein the patch includes a continuous or interrupted ring at an outlying border of the textile, wherein the continuous or interrupted ring reinforces the outlying border of the textile.

9. The implant of claim 8, wherein the ring is formed of an unoriented P4HB fiber extrudate.

10. The implant of claim 1, wherein at least one of the first or second exposed surfaces is convex, and wherein the other of the first or second exposed surfaces is concave.

11. The implant of claim 1, wherein the patch is shaped to conform to inguinal anatomy.

12. The implant of claim 1, wherein the patch has one or more of the following properties:
   (i) a suture pullout strength of at least 10 N;
   (ii) a burst strength of at least 1 Kg;
   (iii) pore diameters of at least 50 µm; and
   (iv) a Taber stiffness that is less than 100 Taber stiffness units.

13. A porous implant consisting of:
a self-anchoring patch to position over a muscle or tissue wall defect, the patch comprising a textile fabricated with first and second fibers of poly-4-hydroxybutyrate or copolymer thereof, and wherein the first fiber used to fabricate the patch is stiffer than the second fiber used to fabricate the patch, the textile having a first side and a second side, wherein the first fiber is on at least one of the first side and the second side of the textile, wherein the first fiber is configured to self-anchor the patch to muscle or tissue, wherein at least one of a surface of the first or second side is convex, wherein the other of a surface of the first or second side is concave, and wherein the patch is shaped to conform to inguinal anatomy.

14. A porous implant consisting of:
a self-anchoring patch to position over a muscle or tissue wall defect, the patch comprising a textile fabricated with first and second fibers of poly-4-hydroxybutyrate or copolymer thereof, and wherein the first fiber used to fabricate the patch is stiffer than the second fiber used to fabricate the patch, the textile having a first side and a second side, wherein the first fiber is on at least one of the first side and the second side of the textile, wherein the first fiber is configured to self-anchor the patch to muscle or tissue, wherein the patch has one or more of the following properties:
   (i) a suture pullout strength of at least 10 N (2.248 lbf); and
   (ii) a burst strength of at least 1 Kg (2.204 lbf).

15. The porous implant of claim 14, wherein the patch has one or more of the following properties:
   (i) pore diameters of at least 50 µm; and
   (ii) a Taber stiffness that is less than 100 Taber stiffness units.

* * * * *